(12) United States Patent
Monicelli

(10) Patent No.: US 8,845,331 B2
(45) Date of Patent: Sep. 30, 2014

(54) METHOD FOR PRODUCING A DENTAL IMPRESSION TRAY

(76) Inventor: Antonio Monicelli, San Giovanni alla Vena-Vicopisano (IT)

( * ) Notice: Subject to any disclaimer, the term of this patent is extended or adjusted under 35 U.S.C. 154(b) by 713 days.

(21) Appl. No.: 12/527,949

(22) PCT Filed: Feb. 22, 2008

(86) PCT No.: PCT/IB2008/000401
§ 371 (c)(1),
(2), (4) Date: Aug. 20, 2009

(87) PCT Pub. No.: WO2008/102251
PCT Pub. Date: Aug. 28, 2008

(65) Prior Publication Data
US 2010/0035211 A1    Feb. 11, 2010

(30) Foreign Application Priority Data
Feb. 23, 2007 (IT) .................. PI2007A0016

(51) Int. Cl.
*A61C 9/00* (2006.01)

(52) U.S. Cl.
CPC .................................... *A61C 9/0006* (2013.01)
USPC .......................................................... 433/214

(58) Field of Classification Search
USPC ................... 433/215, 140, 217.1, 228.1, 223,
433/34–48, 213, 214; 264/16, 219, 322,
264/339; 219/620, 600, 621, 623, 622, 624,
219/625, 626, 627
See application file for complete search history.

(56) References Cited

U.S. PATENT DOCUMENTS

| | | | | |
|---|---|---|---|---|
| 4,401,616 A * | 8/1983 | Wagner | .......................... | 264/138 |
| 4,569,342 A * | 2/1986 | von Nostitz | .................... | 128/862 |
| 6,364,665 B1 * | 4/2002 | Trettenero | ...................... | 433/215 |
| 6,683,587 B2 * | 1/2004 | Gulsen | .............................. | 345/38 |
| 6,749,428 B2 * | 6/2004 | DiMarino et al. | ............... | 433/38 |
| 7,619,188 B2 * | 11/2009 | Oghafua et al. | ............... | 219/620 |
| 2005/0181334 A1 * | 8/2005 | Jacobs | ............................ | 433/215 |
| 2006/0105289 A1 | 5/2006 | Wagner | | |
| 2007/0037116 A1 | 2/2007 | Knutson | | |

* cited by examiner

*Primary Examiner* — Cris L Rodriguez
*Assistant Examiner* — Mirayda A Aponte
(74) *Attorney, Agent, or Firm* — Ladas & Parry LLP

(57) ABSTRACT

A kit to make an individual impression tray for dental use, the kit having a standard model reproducing a dental arch, a semifinished product of thermoformable material, for example, a plate member, and a container for a heat exchange liquid. The first step that is carried out by the dentist to obtain the individual impression tray provides the insertion of the model in the container. Then, next to dental arch of the model a plate member is arranged and hereafter a certain amount of a liquid is put, for example, water, in the container up to covering plate member. The liquid is then heated by a source of thermal power, for example, a microwave oven, stopping heating when the temperature of the liquid achieves a value T* higher than the temperature for softening the thermoformable material of the plate member.

24 Claims, 12 Drawing Sheets

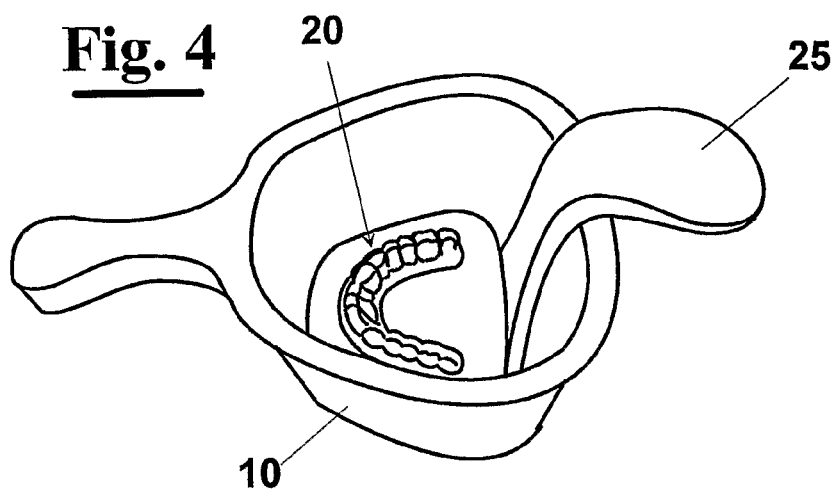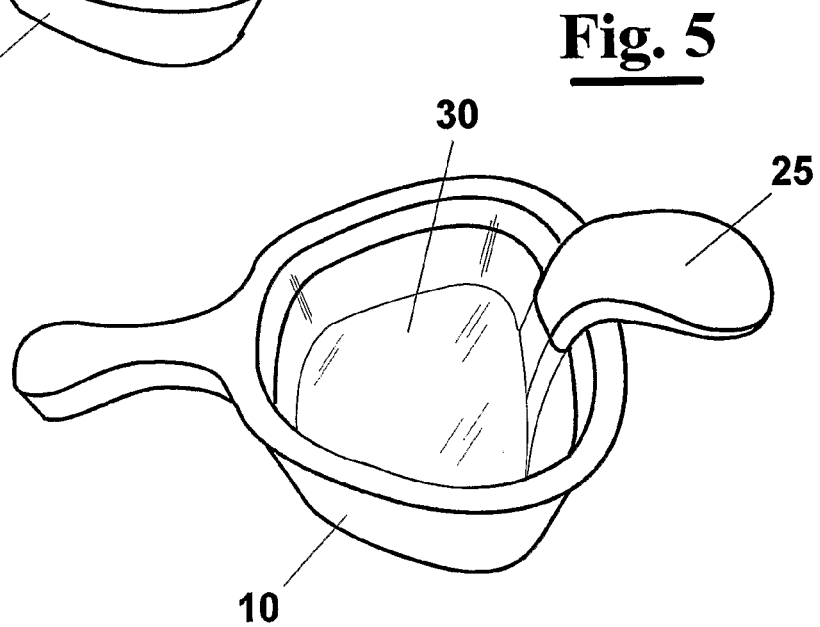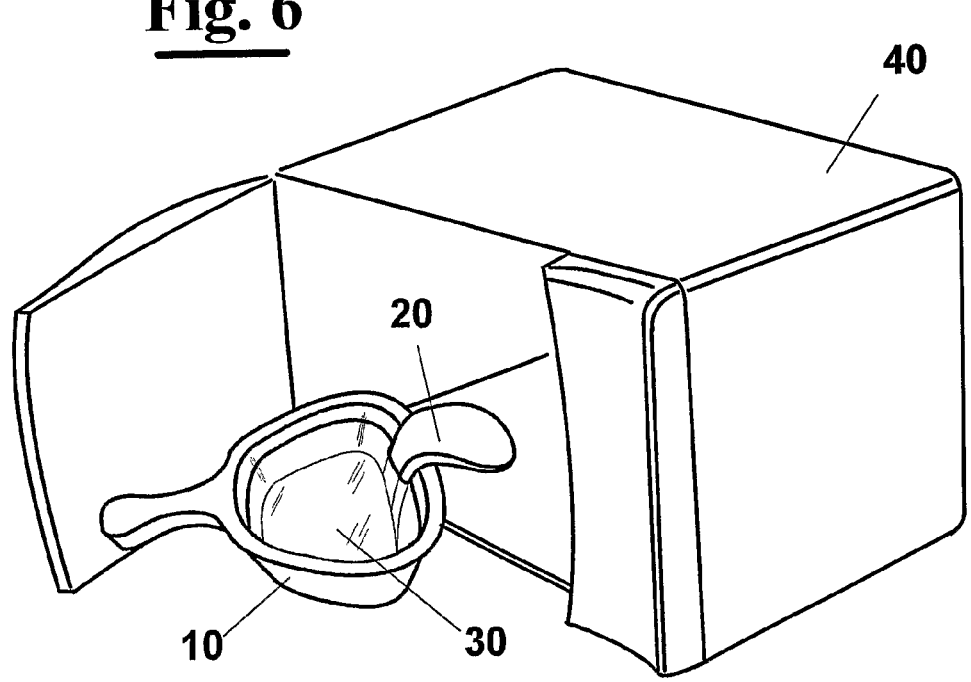

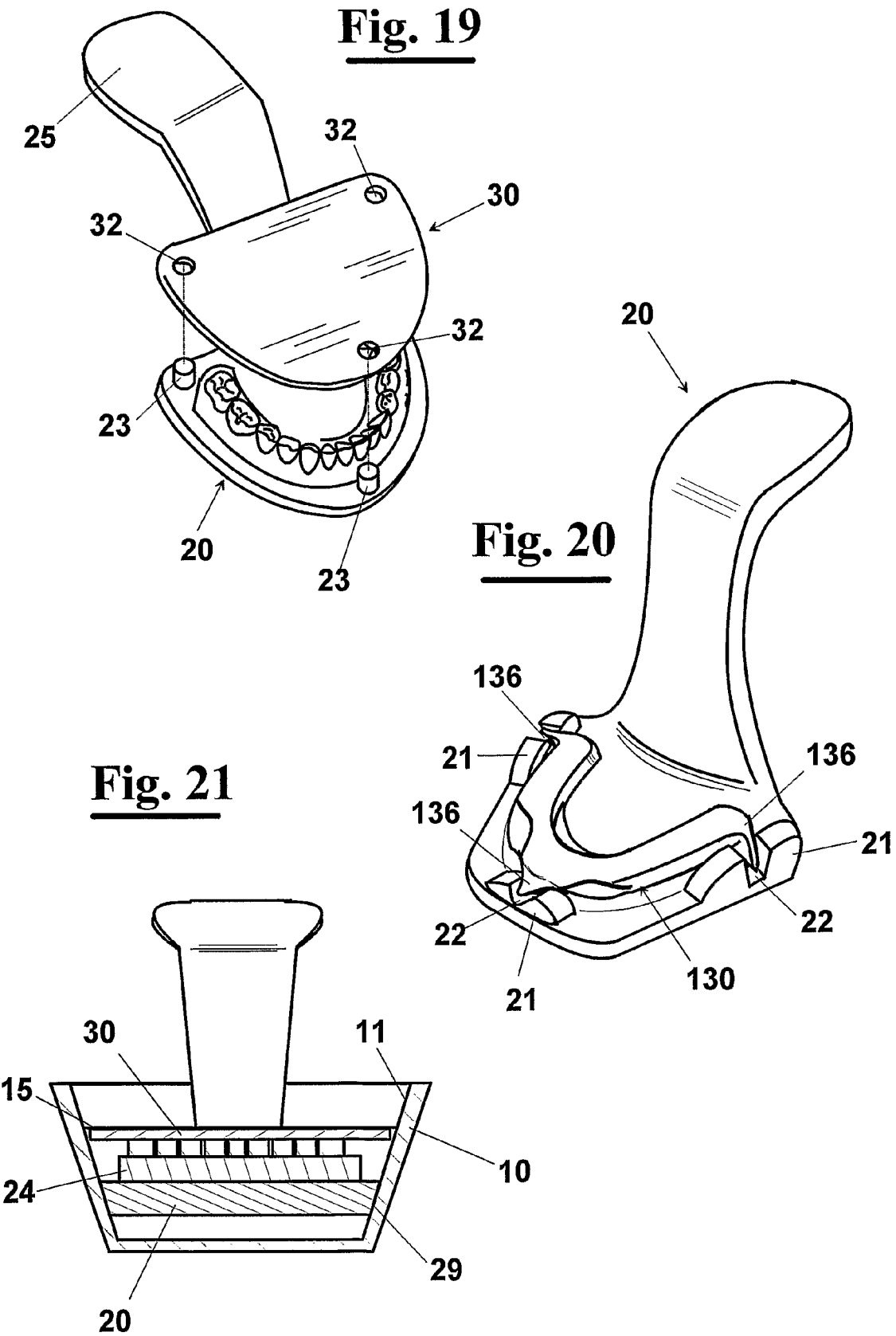

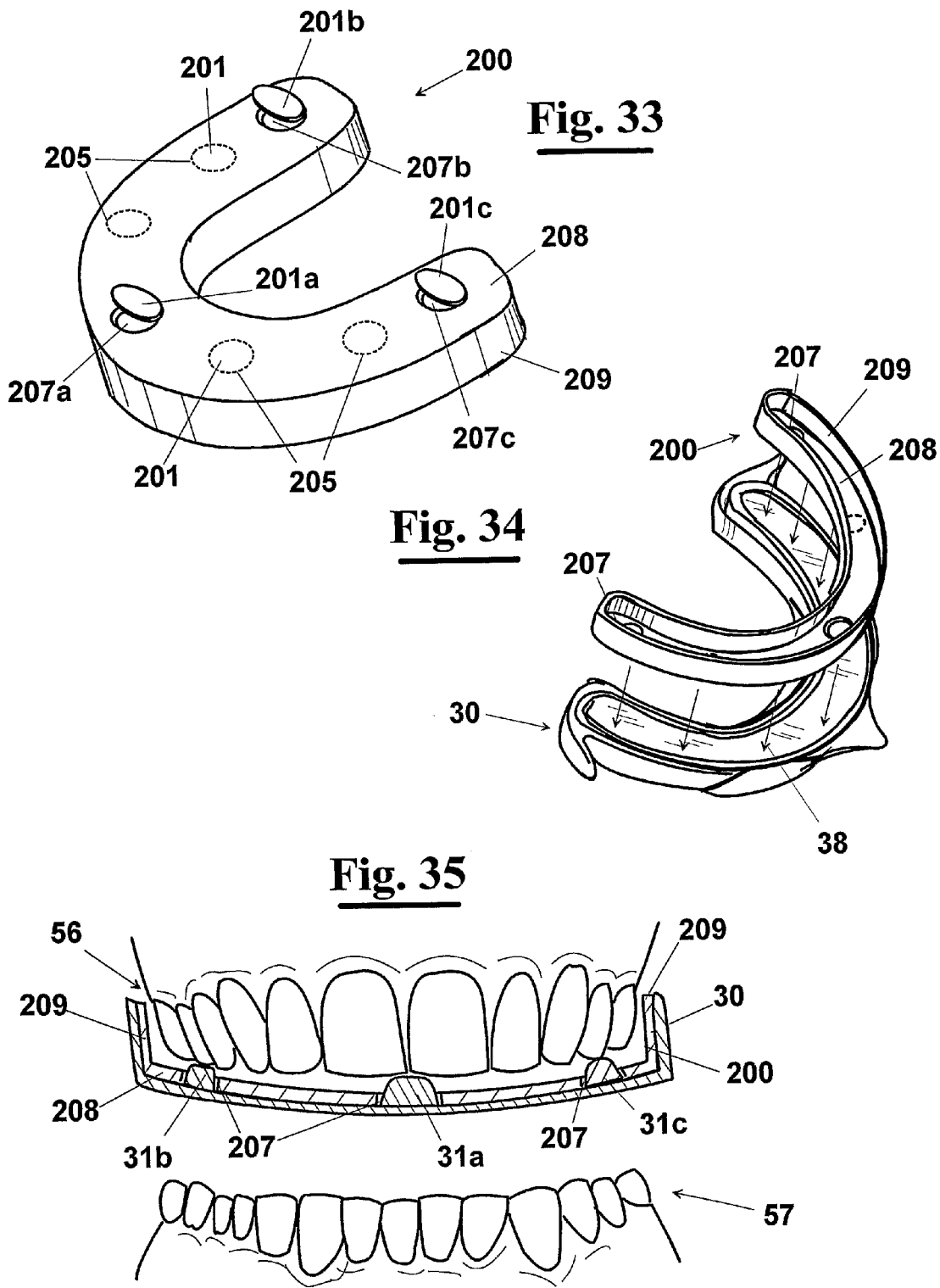

METHOD FOR PRODUCING A DENTAL IMPRESSION TRAY

FIELD OF THE INVENTION

The present invention relates to a method for making an impression tray, in particular, of the individual type, used for measuring the impression of a dental arch of a patient.

DESCRIPTION OF THE PRIOR ART

As well known, a variety exists of types of impression trays commonly used by the specialists of the dental field for obtaining an impression of a dental arch of the patients that, for aesthetic or functional reasons, need a dental treatment.

Normally, an impression tray is made of metal, or of plastic material, and have U-shaped cross section.

The operation of obtaining dental impression provides putting an impression material in the impression tray which is in turn inserted in the mouth of a patient. The plastic impression material, turning into a solid state starting from a viscous state, is moulded taking the shape of a dental arch. The impression material eventually hardens producing a strong grip on the teeth of the patient. Therefore, during the removal of the impression tray from the mouth of the patient it is necessary that dentist exerts a high force at a handgrip of the tray. This stresses too much a part of the material causing irreversible deformation that affects the final shape of the gypsum model. As a consequence of this, the position and orientation of the teeth of the patient are determined in a not precise way.

Furthermore, since the morphologic features and the size of the mouth are different for each patient, it is necessary to provide impression trays having different size.

Techniques are also known to provide custom impression trays made to measure.

For example, in U.S. Pat. No. 4,401,616 a method is described that provides heating a sheet of thermoplastic material up to a softening temperature at which it reaches a deformable state. The thermoplastic material can be thus shaped on a standard gypsum model of a dental arch and then cooled up to a stiff status in order to form the custom impression tray.

However, the heated thermoplastic material used to provide the impression tray through the process above described remains for not much time in the softened status that is deformable. Therefore, it is necessary to heat many times the material during the shaping steps on the model, in a difficult and slow process.

Furthermore, gypsum is a porous and hygroscopic material and therefore cannot be kept into contact of the sheet of thermoplastic material when this is hot, or humid, since the model would "crumble", i.e. to ruin, jeopardizing the hygienic conditions necessary for dental operation. On the other hand, when the sheet of thermoplastic material is located at a low temperature it is not possible to shape it. Therefore, it is necessary to bring the sheet of thermoplastic material to a precise temperature of compromise, that can be set in a difficult way, and in any case kept for not much time. All this makes extremely complex to work on the sheet of thermoplastic material to obtain the individual impression tray.

In addition, the gesso, always owing to its high hygroscopicity, cannot be sterilized in autoclave. Therefore, for sanitary reasons a same gypsum model cannot be used more than once.

An example of method for making an individual "tray" for containing dental substances for customized treatments is described in US2005/0181334.

In particular, US2005/0181334 describes a method for making an individual "tray" of flexible and resilient type assisting dentist during specific dental treatments that relate to exclusively the external surface of the teeth, such as teeth whitening treatments. The choice of using highly flexible and resilient thermoplastic material to provide the tray is explained by the need to minimize as far as possible the thickness of the whitening or fluoride gel used and for then easily removing it from the mouth once ended the treatment. The aim of US2005/0181334 is a flexible containing tray to assist a treatment to the teeth. The individual "tray" allows then to maximize the penetration of the whitening or fluoride gel for adhering correctly, even to undercut portions, thanks to its features of high flexibility and elasticity.

On the other hand, it is desirable that an impression tray is made of a non-deformable and highly stiff material, capable of resisting even to strong actions, in particular, to the strong forces of the impression material in operative conditions. For achieving this result, however, it is not possible to use the tray described in US2005/0181334 as individual impression tray.

SUMMARY OF THE INVENTION

It is then a feature of the present invention to provide a method for making an individual impression tray that is easy and quick to be used by a specialist.

It is another feature of the present invention to provide such a method for reducing the amount of material that can be used for obtaining the impression of the patient and allows then high savings with respect to the existing techniques.

These and other features are accomplished with one exemplary method for making an impression tray for obtaining an impression of a dental arch, according to the present invention, whose main feature is that it comprises the following steps:

arranging in a container of:
  a model of heat-resistant material reproducing a dental arch;
  a semifinished product of thermoformable material located above the model at the dental arch;
  a heat-transmission fluid such that the model and the semifinished product are dipped in said fluid;
softening the thermoformable material of said semifinished product by heating said fluid at a temperature T* higher than the softening temperature of said material, said softening step causing the semifinished product to become thermoformed on the model obtaining a recess on the side of the semifinished product next to dental arch of the model and a protrusion on the opposite side;
cooling the thermoformable material.

Preferably, the semifinished product can be finished, before the end of said cooling step, modelling it directly on the dental arch of the patient obtaining an individual impression tray.

The semifinished product can be also finished on the dental arch of the patient after the end of the cooling step, through a new softening step of the thermoformable material.

Advantageously, the model has a handgrip adapted to assist the grip by the specialist, said handgrip, in use, protruding from the container or emerging from the fluid. More in detail, the handgrip is bent outwards of the container in order to avoid to encounter the vapour rising from the hot fluid.

In particular, the dental arch of the model comprises a plurality of templates that are oversized 20%-30% with respect to the average anatomical size. This way, the impression material can be easily put in the impression tray without, however, using an excessive amount of the impression material. Furthermore, the teeth of the model are oversized to allow using the impression tray for mouths having different size and independently from belonging to the lower or the upper dental arch.

Advantageously, the heat-resistant material of the model is a low thermal conductivity material. In particular, the low thermal conductivity material forms a thermal barrier, since it produces a not uniform heat distribution on the model that is therefore hotter in the portion dipped in the fluid, causing the semifinished product to soften, and colder in the emerging portion. This allows then gripping easily the handgrip of the model for extracting the thermoformed semifinished product of the impression tray and to subject it to further works.

Preferably, the heat-resistant material of the model is selected from the group comprised of: a ceramic material and a glass material. A ceramic material, in fact, have a low thermal expansion, high tolerance to temperature, low dielectric constant, stiffness and dimensional stability. The choice of the ceramic material allows, furthermore, using the model many times, since it is possible to sterilize it easily in autoclave like other dental tools not belonging to the class of disposable products.

In particular, on the impression tray can be made at least one wing protruding from the external side surface and adapted to provide a gripping point for the specialist.

Preferably, a first wing protruding at a portion in front of the incisors, a second wing at a portion in front of the right molars and a third wing at a portion in front of the left molars.

More in detail, when removing the impression tray with the impression material hardened inside, the specialist, acting on the wings protruding from the external side surface, causes a disengagement of the corresponding portions of the impression tray from the dental arch of the patient. This causes air to enter between the inner surface of the impression tray and the dental arch of the patient assisting the removal of the impression tray. The protruding wings, furthermore, avoids making traditional handgrips for the impression tray. Therefore, the vertical encumbrance of the impression tray is remarkably reduced, such that two impression trays can be used at the same time, one for the upper dental arch and one for the lower dental arch for obtaining the respective dental impressions, without that the two impression tray interfere with each other.

Advantageously, a step is provided of making a stiffening bead obtained folding the borders of the semifinished product. In particular, the stiffening bead can be made both at the front portion and at the rear portion of the impression tray.

For example, at the front stiffening bead the thickness of the impression tray can be about twice the original, whereas at the rear portion the thickness of the impression tray can be about three times the original.

Advantageously, at the projection of the thermoformed semifinished product lateral containing edges are made. This way, with a single impression tray it is possible to measure both the impression of the agonist dental arch introducing the impression material at the recess, which the impression of the antagonist dental arch introducing impression material between the containing edges.

Advantageously, the semifinished product of thermoplastic material is a uniform thickness plate member, which can be U-shaped.

Alternatively, the semifinished product can be a pre-printed semifinished product substantially U-shaped and having a recess on one side and a corresponding projection on the opposite side.

In this case, the pre-printed semifinished product can have wings protruding outside and/or of lateral containing edges at the projection. Alternatively, the wings and the containing edges can be made in a second moment i.e. after having caused the material to soften.

In particular, in case of the plate member this may have a thickness set between 0.5 and 10 mm, advantageously between 1 and 4 mm.

Advantageously, the pre-printed semifinished product can be put again for a few instants in the heated fluid in order to cause it to soften again in order to complete the modelling step.

In particular, the thermal power source can be a microwave oven with power set between 600 and 2000 watt, advantageously 800 watt. In this way problems inherent to the work of the dentist hereafter described.

Firstly, the need is felt of having hot water quickly and at an uniform temperature. The microwave oven heats uniformly the content causing the water molecules to friction with each other, whereas a different source, such as an electric resistance, heats only the water at direct contact, and in case the temperature has to be made uniform quickly a recirculation system of the fluid should be put in the container, with additional costs and complications. With the use of a microwave oven the desired temperature is obtained on average in about 60 seconds.

Furthermore, the need is felt of assuring high hygienic conditions. In case of the microwave oven the heat source is not dipped in the fluid and must not then be sterilized after each use. In addition, it is easy to sterilize only the liquid container once used, not hampered by other devices. The microwave oven same has also a disinfecting action disintegrating the bacteria.

Another aspect is the operative safety. The microwave oven is turned on only when needed; if a resistance is used in order to limit the waiting time it should be always turned on, and this would cause deposit of limestone in the container, slowness owing to the frequent change of fluid after the use that initially cold has to be brought to the correct temperature, and risk of overheating especially if it is forgotten turned on when the surgery is closed.

The microwave oven allows, furthermore, limited costs and the need of a minimum space owing to the minimum encumbrance.

Once detected the temperature of the fluid at the source with a small thermometer it is possible to achieve the desired temperature in a time that can be set by the timer of which all the microwave ovens are equipped with, since the volume of the fluid, power and time of microwave irradiation are known.

Advantageously, before finishing the semifinished product of thermoformable material by modelling it on the dental arch of the patient a step is provided of spraying a surfactant on the dental arch.

According to another aspect of the invention, a dental kit to provide an impression tray for detecting the impression of a dental arch comprises:
- a standard model of heat-resistant material reproducing a dental arch;
- a semifinished product of thermoformable material adapted to be put on said standard model at said dental arch;
- a container adapted to contain a heat exchange fluid in which said semifinished product and said model are put, for being heated together.

Advantageously, said kit provides a thermal power source adapted to cause said heating up to a temperature of the fluid larger than necessary for softening said thermoformable material.

In particular, the container and the standard model have respective reference surfaces suitable to ensure a precise relative location. More in detail, the container and the standard model may have frustoconical sections that can be mutually coupled.

Advantageously, the standard model and the semifinished product have mutual cooperating means adapted to assist the mutual location.

Advantageously, the thermoformable material is a material for prosthetic bases, in particular, selected from the group comprised of:
  polymethylmethacrylate (PMMA);
  acrylic resins,
  vinyl-acrylic copolymers,
  urethane oligomers,
  shellac, which can be added to a substance selected from the group comprised of: copal, colophony, natural resins and synthetic resins, or a mixture thereof;
  a combination thereof.

Advantageously, the impression tray made as above described has at least one hole. This allows, in particular, to assist the retention of the material and the grip of the impression in the field of dental implants, in particular, if the impression is obtained with an impression transfer of known type.

Furthermore, a spacing element can be provided having a substantially U-shaped base portion and side portions of measured height, said spacing element being adapted, in use, to be located between the dental arch of which an impression has to be obtained and the semifinished product of thermoformable material. This allows to optimize the thickness of the impression material available and/or to insulate thermally the dental arch of the patient of which an impression has to be obtained.

In particular, the spacing element has reference areas arranged at determined points of the dental arch.

More in detail, after having arranged the spacing element on the dental arch of the patient, the operator removes some of said reference areas. Then, the semifinished product brought to a temperature to which it can be modelled is forced to cross the spacing element at the apertures made by removing the reference areas, in order to provide respective projections, or "shoes", at that the semifinished product rests on the dental arch of the patient.

Advantageously, the reference areas are defined by tear-off lines that assist the removal by the operator during the use.

In particular, the spacing element can be made of a material selected from the group comprised of:
  pluriball;
  natural rubber, which can be mixed with other compounds to obtain a compound of the type used for chewing gum;
  tinfoil;
  sheets of polyethylene that can be arranged on the tinfoil to form a sandwich
  sheets of tissue i.e. ALCANTARA® polyester/polyurethane composite textile material.

Advantageously a container is provided having a temperature sensor, for example associated with a liquid crystal display, adapted to measure the temperature of the fluid in it contained and to send a corresponding signal of temperature to control means, said control means being adapted to determine the heating time necessary for bringing the fluid from the starting temperature to a determined temperature T* higher than the temperature for softening said material, by the thermal power source.

The container has, preferably, fluid inlet of size corresponding to a tap from which the fluid is drawn.

Advantageously an auxiliary push element is provided that is arranged, in use, between said impression tray located, with said impression material inside, on the dental arch of which an impression has to be obtained and the other dental arch, said auxiliary push element being pressed when closing the mouth of the patient against the impression tray in order to force the impression material towards the base of the dental arch.

In particular, the auxiliary push element can comprise:
  a hollow bodies adapted to contain at least one tooth, or tooth stump, of the dental arch;
  a push surface on which the dental arch not interested by the impression material acts for pushing said hollow bodies on said impression tray, said push surface and said hollow bodies being pivotally connected to each other;
  a handgrip integral to said hollow bodies and adapted to be gripped by the operator for actuating said hollow bodies.

More in detail, the auxiliary push element increases the push on the impression material towards the base of the tooth, or the teeth, of which an impression has to be obtained. This increases the precision of the impression, in particular, in case of milled teeth, or stumps, made before an artificial article such as a bridge or a crown.

A third aspect of the invention provides a pre-printed semifinished product to make an individual impression tray substantially U-shaped and having a recess on one side and a protrusion on the opposite side, said product providing at least one among:
  an externally protruding wing;
  a lateral containing edge at said projection.

In particular, the pre-printed semifinished product can comprise at least one grip portion that in use remains visible, said grip portion being adapted to keep the impression material during the removal of the impression tray at the end of the step of obtaining the impression of the dental arch of the patient, in order to increase the capacity of retention of the individual impression tray.

Advantageously, the grip portion is made at least at one stiff insert integrated in the thermoformable material and have external not harmful surface for the teeth and the oral tissues of the patient.

In particular, the insert may have a geometry selected from the group comprised of:
  spheric geometry;
  conic geometry;
  toroidal geometry;
  cylindrical geometry;
  prismatic geometry;
  pyramidal geometry;
  ellipsoidal geometry.

In an alternative exemplary embodiment of the invention, the grip portion can be made on portions of sheet of a material selected from the group comprised of:
  woven fabric;
  non woven fabric;
  knitted fabric;
  a material having a determined rate of porosity;
  a combination thereof.

More in detail, the grip portion can be integrated in the semifinished product at the production stage and exposed after sandblast or deposited on the heated surface under warm air or lamps, or alternatively, can be arranged on the semifinished product directly by the operator in phase of finishing after a suitable heating.

According to a fourth aspect of the invention, a method for making a pre-printed semifinished product used to make an individual impression tray comprises the steps of:
- arranging a mould equipped with:
  - a first half having a substantially U-shaped housing;
  - a second half equipped with a projection which is also substantially U-shaped, said first and said second half being in use overlapped in order to arrange said projection at said housing;
- introducing a thermoformable material in the molten state in said housing;
- cooling said molten material with subsequent hardening thereof;
- extracting said pre-printed semifinished product from said housing;

said housing having at least one side appendix at which the thermoformable material, once hardened, forms a corresponding externally protruding wing that protrudes from said pre-printed semifinished product extracted from said mould.

Advantageously, before that said cooling step of said thermoformable material is completed a step is provided of:
- arranging a retention element having a grip portion for said impression material, said grip portion remaining visible in said pre-printed semifinished product.

In particular, said retention element is selected from the group comprised of:
- a stiff insert having external surface not harmful for teeth and oral tissues of the patient;
- a sheet of a material selected from the group comprised of:
  - woven fabric;
  - non woven fabric;
  - knitted fabric;
  - a material having a determined rate of porosity;
  - a combination thereof Furthermore, a step can be provided of finishing of said pre-printed semifinished product extracted from said mould, said finishing step being adapted to provide a partial emerging of said insert from said pre-printed semifinished product.

In particular, before being subject to the moulding process to obtain said pre-printed semifinished product, the thermoformable material is mixed to a determined amount of a substance selected from the group comprised of:
- an adhesive substance;
- an impression material.

According to a fifth aspect of the invention, a mould to prepare a pre-printed semifinished product to provide an individual impression tray, through a moulding process of a thermoformable material comprises:
- a first half equipped with a substantially U-shaped housing;
- a second half equipped with a projection which is also substantially U-shaped, said projection being arranged in use at said housing;
- said housing having at least one protruding portion at which the thermoformable material, once hardened, forms a corresponding externally protruding wing that protrudes from said pre-printed semifinished product.

In an impression technique in implantology by an impression transfer where the use of the individual impression tray is compulsory and not optional, the present invention allows eliminating a first step relative to the impression in alginate or similar material, a second step relative to casting the gypsum model and a third step relative to the construction of an individual impression tray pierced by an dental technician. The first two steps are eliminated and the patient saves going a preliminary time to the dentist's surgery; the third step is carried out directly by dentist in one session and not by the dental technician in three sessions. With the present invention dentist makes immediately the individual pierced impression tray where to block the impression transfer is housed at the first session with the patient.

The present invention can be applied advantageously also in the orthodontic field where the first impression, in particular in processes of construction of serial computer-aided templates must result as exact as possible with respect to the original. The precision of the present invention is advantageous for the successive steps reducing the risks of error and of repeating the first impression.

BRIEF DESCRIPTION OF THE DRAWINGS

The invention will be made clearer with the following description of an exemplary embodiment thereof, exemplifying but not limitative, with reference to the attached drawings wherein:

FIGS. 4 to 10 show diagrammatically a possible succession of steps through which it is possible to provide an impression tray, in particular, an individual impression tray, according to the invention;

FIGS. 18 and 20 show a perspective view of a further exemplary embodiment for the model of FIG. 1;

FIG. 19 shows a perspective view of other exemplary embodiments for the semifinished product and for the model of FIG. 1;

FIG. 21 shows a cross sectional view of a particular shape of the model and of the container that allows a precise autocentering assembly;

FIGS. 33 to 35 show a spacing element that is put between the dental arch of the patient and the impression tray, according to the invention.

DESCRIPTION OF PREFERRED EXEMPLARY EMBODIMENTS

Figure 1:
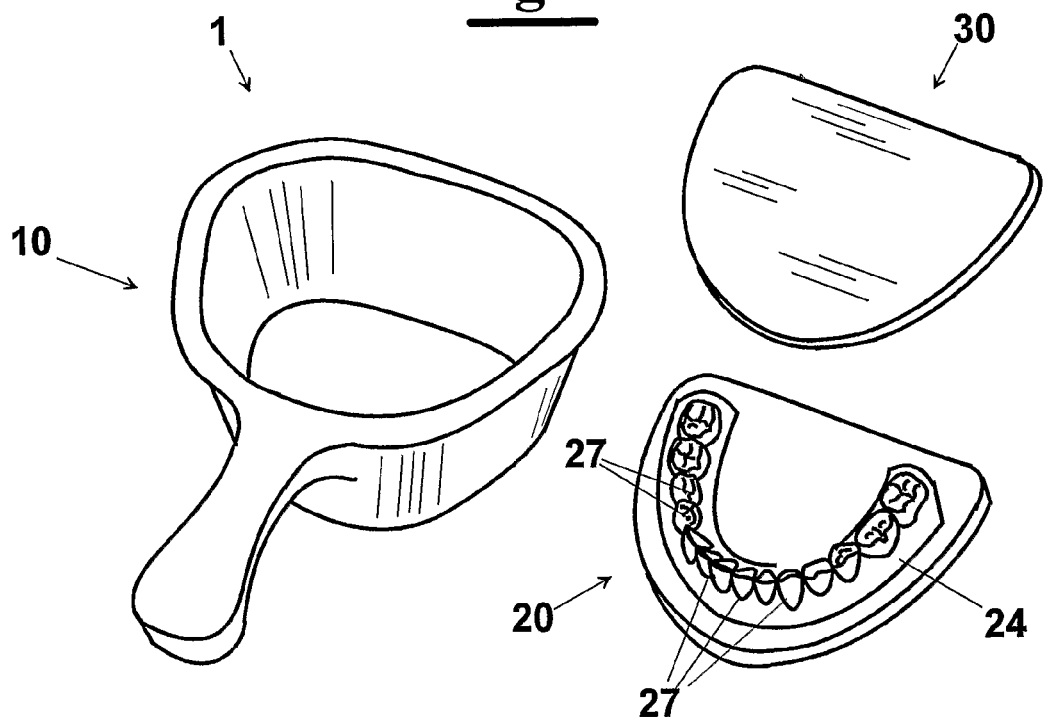
FIG. 1 shows a perspective view of the essential elements of a kit to provide an impression tray, according to the invention.

With reference to FIG. 1, a kit 1 to make an individual impression tray for dental use comprises essentially a standard model 20 reproducing a dental arch 24, a semifinished product of thermoformable material, for example a plate member 30, and a container 10 for a heat-transmission fluid (FIG. 1).

The first step that can be carried out by a dentist 60 to provide the individual impression tray 100 provides the insertion of model 20 in container 10. Then, next to the dental arch of model 20 plate member 30 is located and hereafter put in a certain amount of a fluid 15, for example water, in container 10, up to cover plate member 30.

Figure 7:
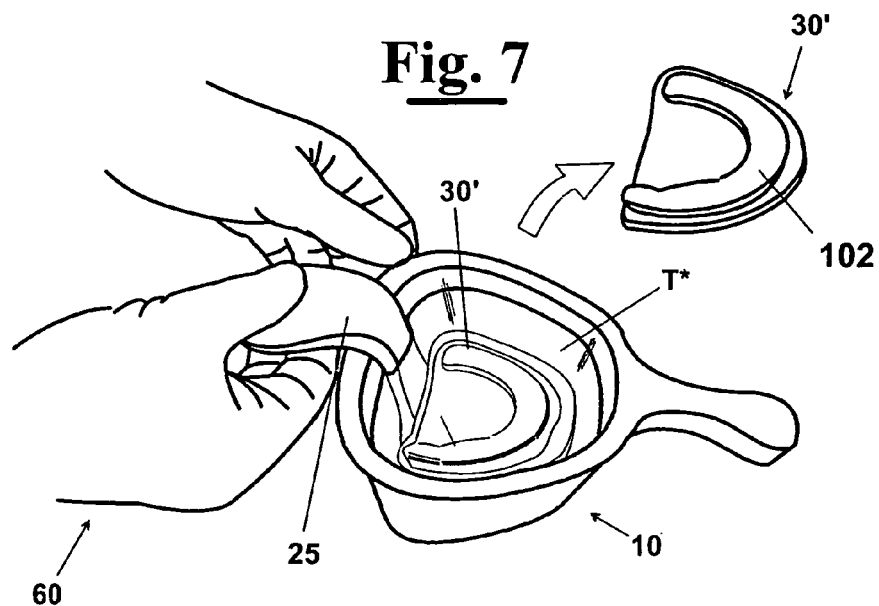
Figure 9:
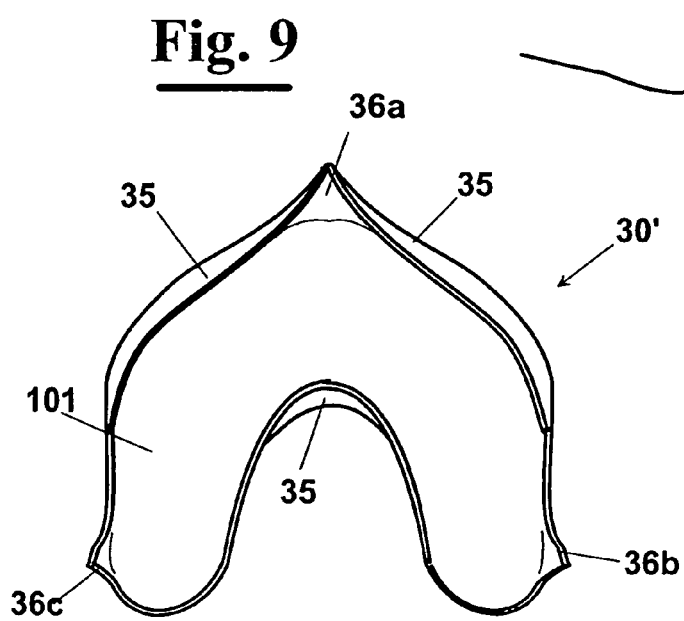

The fluid 15 is then heated by a source of thermal power, preferably a microwave oven 40 (FIG. 6). The heating step is stopped when the temperature of the fluid 15 achieves a value T* higher than the temperature for softening the thermoformable material of plate member 30. At temperature T*, plate member 30 of thermoformable material is in a gummy state and therefore collapses on the standard model 20, assuming substantially its shape, obtaining a thermoformed plate member 30' equipped with a recess 101, at the side facing model 20, and with a corresponding projection 102, at the opposite side (FIGS. 7 and 9). If the fluid 15 is water, the heating step can be stopped when the temperature of the fluid T* is about 80° C. The temperature of the fluid 15 can be advantageously monitored continuously by a thermocouple, or other temperature sensor, not shown in the figure.

Figure 2:
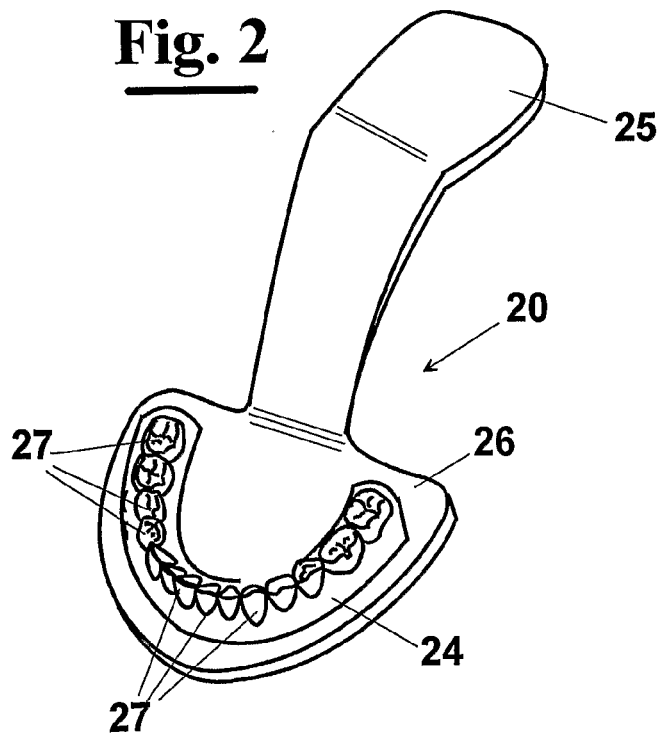
FIG. 2 shows a perspective view of a possible exemplary embodiment for a standard model of the kit of FIG. 1.

In a preferred exemplary embodiment, the standard model 20 has a handgrip 25 adapted to assist the grip of dentist 60 (FIG. 2). More in detail, the handgrip 25 is bent outwards of container 10 in order to avoid to encounter the vapour rising from the fluid during the heating step.

Model 20, furthermore, is made of a low thermal conductivity material, preferably ceramics, so that it has a heterogeneous heat distribution. Therefore, model 20 is much hotter at a portion dipped in the fluid 15 and colder at the handgrip 25, which in operative conditions protrudes from container 10 (FIG. 5).

Figure 3:
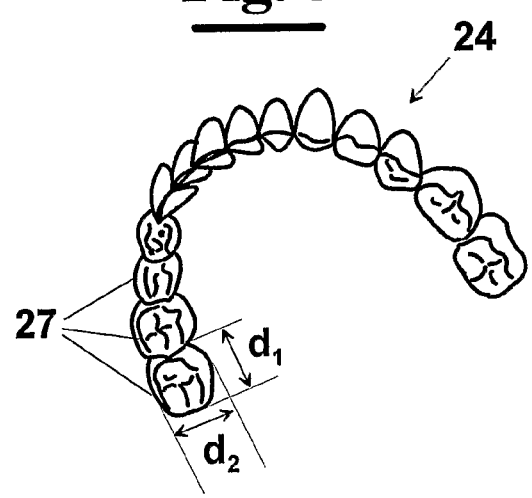
FIG. 3 shows diagrammatically in detail the dental arch reproduced on the model of FIG. 1.
Figure 13:
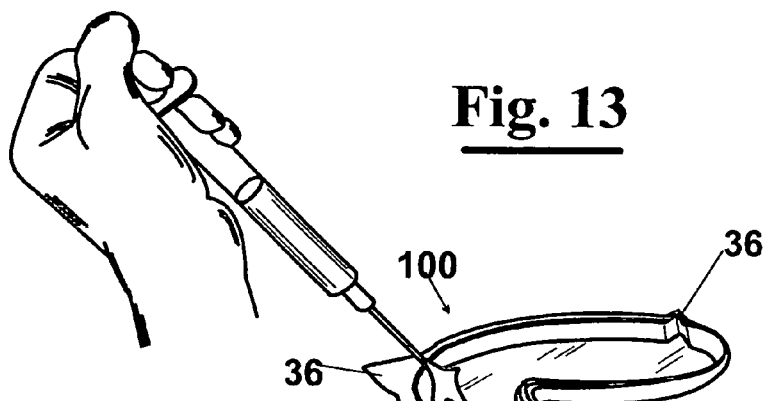
FIGS. 13 and 14 show diagrammatically two instants of obtaining an impression of a dental arch with the impression tray of FIG. 11.

In particular, the dental arch 24 of model 20 comprises a plurality of templates of teeth 27 having size (d1 and d2) larger about 20%-30% than the average anatomic size (FIG. 3). Therefore, impression tray 100 is also oversized so that a free volume is available in which the impression material can be inserted (FIG. 13). Then, impression tray 100 is put in the mouth 52 of the patient at the upper, or lower, dental arch. Model 20 and plate member 30 can be selected among a plurality of items of different size.

Figure 8:
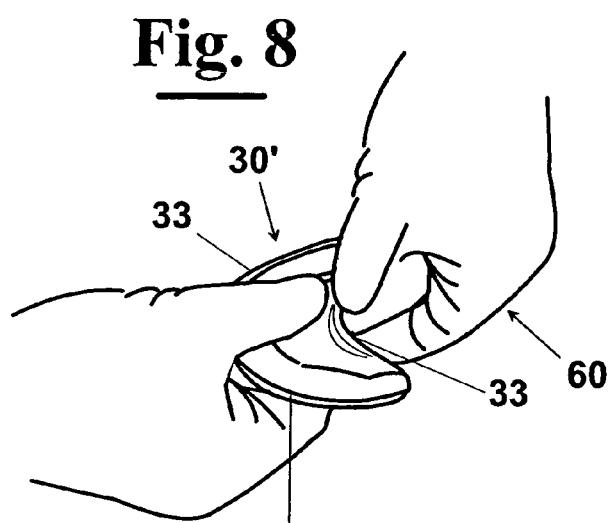
Figure 12:
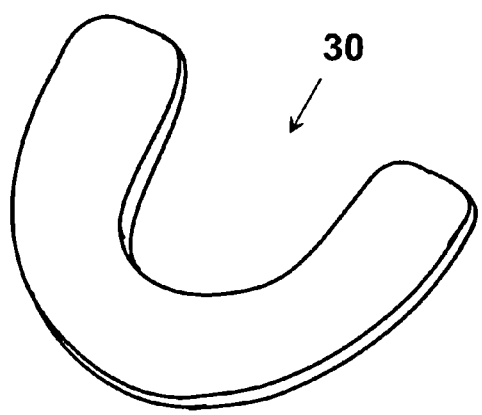
FIG. 12 shows a possible exemplary embodiment of the semifinished product of FIG. 1.

Thermoformed plate member 30' is then further worked by hand by the dentist 60 for modelling it substantially U-shaped (FIG. 8). Alternatively, plate member 30 can be supplied already U-shaped from the beginning (FIG. 12).

Figure 10:
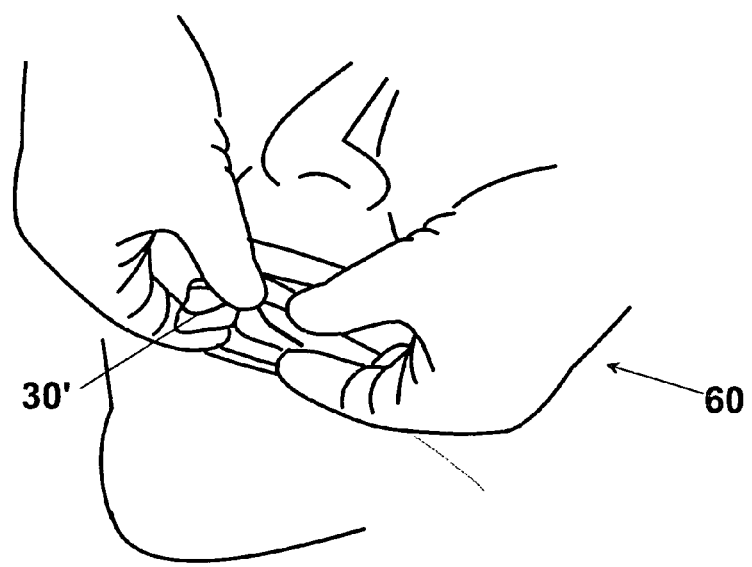
Figure 11:
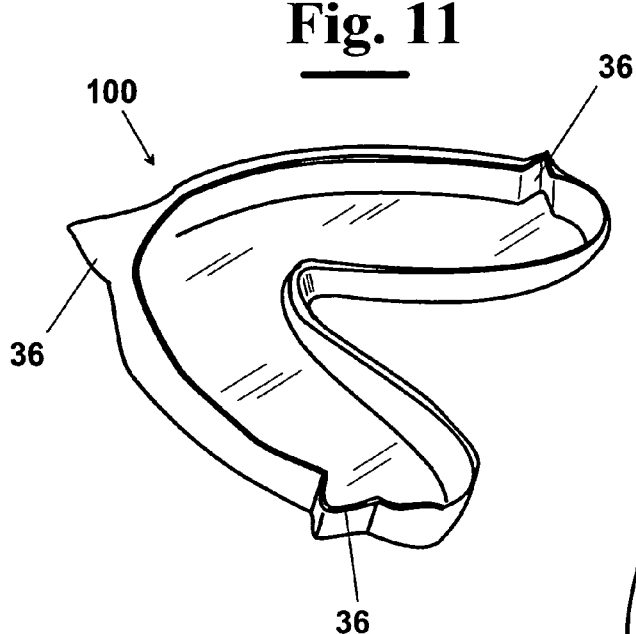
FIG. 11 shows an individual impression tray made through the succession of steps shown in figures from 4 to the 10.

Before ending the modelling step directly in the mouth 52 of the patient, in order to achieve a customized morphology (FIG. 10), obtaining the individual impression tray 100 shown in FIG. 11, the thermoformed plate member 30' can be also bent at points 33 to form stiffening beads 35 (FIG. 9). Furthermore, on the side surface of plate member 30' externally protruding wings 36 can be also made, for example a first wing 36a made at a portion in front of the incisors, a second wing 36b made at a portion in front of the right molars and a third wing 36c made at a portion in front of the left molars.

Figure 14:
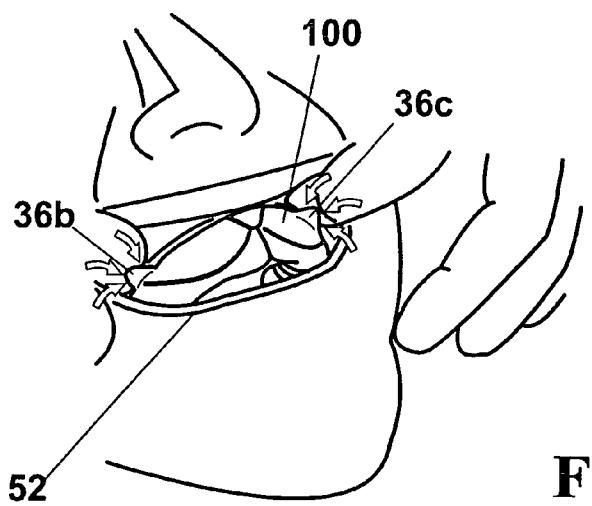

In particular, protruding wings 36a-36c can be used by dentist 60 as maneuvering grips when removing impression tray 100 with the impression material hardened inside (FIG. 14). More in detail, acting on wings 36b and 36c, dentist 60 causes the corresponding portions of impression tray 100 to detach slightly from the dental arch 55 of the patient. This way, air 70 is allowed to enter between the inner surface of impression tray 100 and the dental arch 55 of the patient. This avoids the creation of a suction force assisting the removal of impression tray 100 from the mouth 52, without forcing impression tray 100 with the risk of deforming it and negatively affecting the impression.

Figure 15A:
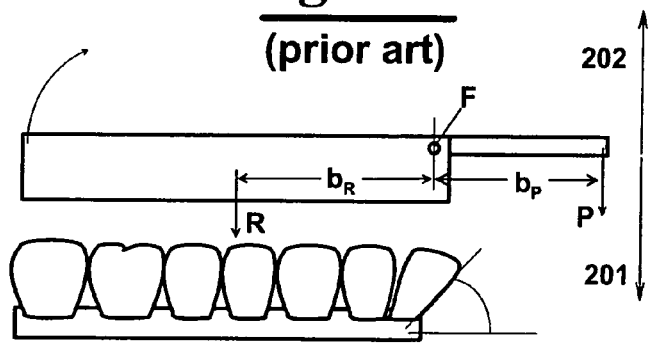
FIGS. 15A and 15B show diagrammatically elevational side views of the moment of the removal of the impression tray respectively in case of a traditional impression tray and of an impression tray according to the invention.
Figure 15B:
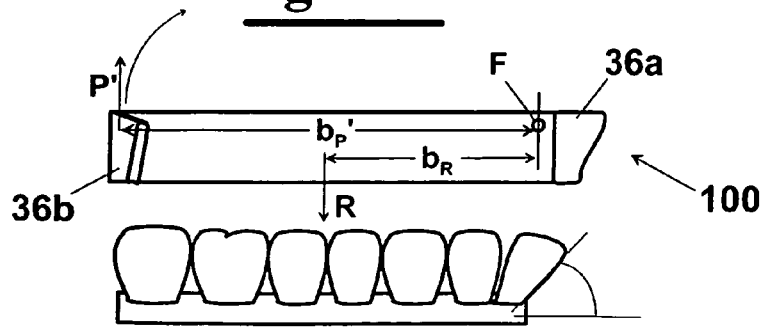

Traditionally, in fact, when removing the impression tray with the impression material hardened inside, the main obstacle that opposes to removing the impression tray is the grip of the impression material hardened on the dental arch of the patient, as shown by the undercut portion, indicated as angle $\alpha$ in FIGS. 15A and 15B, formed by the incisors in the zone next the lips. As shown in detail always in FIG. 15A, when removing the tray, the dentist must act on the handgrip of the impression tray with a high force P, normally incontrollable, both in the direction of removal 201 and in the opposite direction 202, in order to exceed the resistance R of the impression material hardened on the dental arch and to exceed the obstacle consisting of the incisors at which arm $b_P$ is fulcrated. The force P of the dentist is therefore high, since the lever of the species that is obtained is normally of disadvantageous type ($b_P < b_R$).

For removing, instead, an impression tray 100, according to the invention, it is enough to apply a reduced force P' at the rear wings 36b and 36c, since the lever that is obtained is of II species (force resistive set between fulcrum and applied force P), which is always advantageous. In addition, it is possible to apply the force P' directly in the direction 202 that exceeds the incisors.

Since the thermoformable material remains plastic for a certain time after its removal from the source of thermal power, the shape and the position of wings 36, in particular, of the rear wings arranged at the molar of the patient, adapt to the morphologic features of the mouth, in order not to interfere with the muscles of the cheek and with a lip of the patient.

Figure 16:
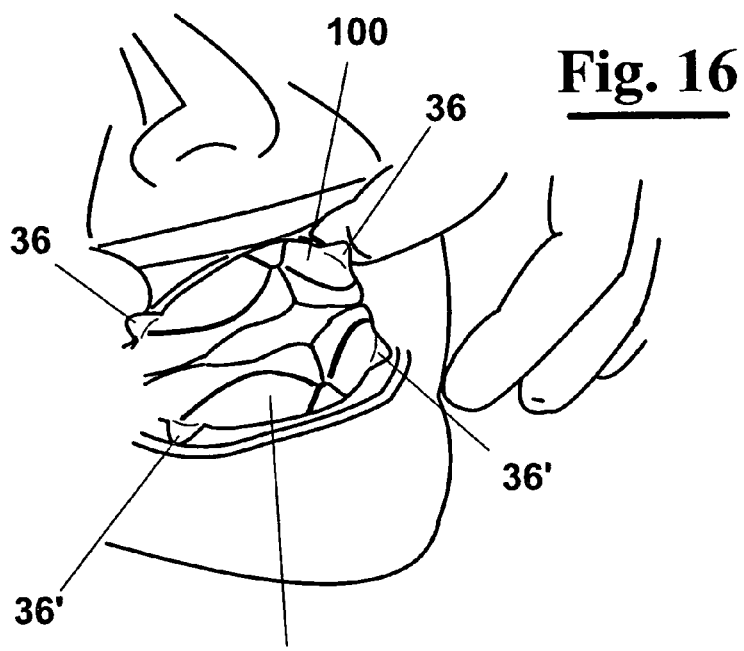
FIG. 16 shows diagrammatically the possibility of taking at a same time the impression of the two dental arches of a patient by the impression tray of FIG. 11.

The absence of the traditional handgrip for impression tray 100, having only wings 36 as gripping points for dentist 60, allows also of reducing the overall vertical encumbrance. Therefore, dentist 60 can use at the same time two impression trays 100 and 100', one for measuring the impression of the upper dental arch and one for the lower dental arch, with savings with respect to traditional techniques (FIG. 16).

Figure 17:
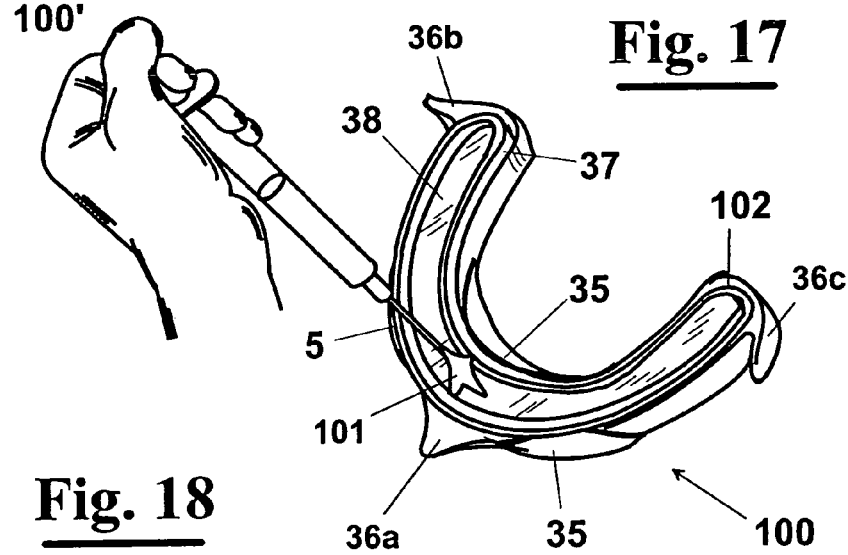
FIG. 17 shows a perspective view of a possible exemplary embodiment of the impression tray of FIG. 11.

At the projection 102 of impression tray 100 containing edges 37 can be made (FIG. 17). This way, it is possible to use a single impression tray 100 for obtaining both the impression of the agonist dental arch introducing the impression material in recess 101, and the impression of the antagonist dental arch, introducing the impression material in recess 38 defined by the containing edges 37.

In an advantageous exemplary embodiment, as starting semifinished product it is possible to use a pre-printed semifinished product 130 (FIG. 20). Like above described for plate member 30, article 130 rests on model 20 and the heating fluid contained in container 10 is put in, being then subject to the process of softening necessary to provide impression tray 100.

Figure 18:
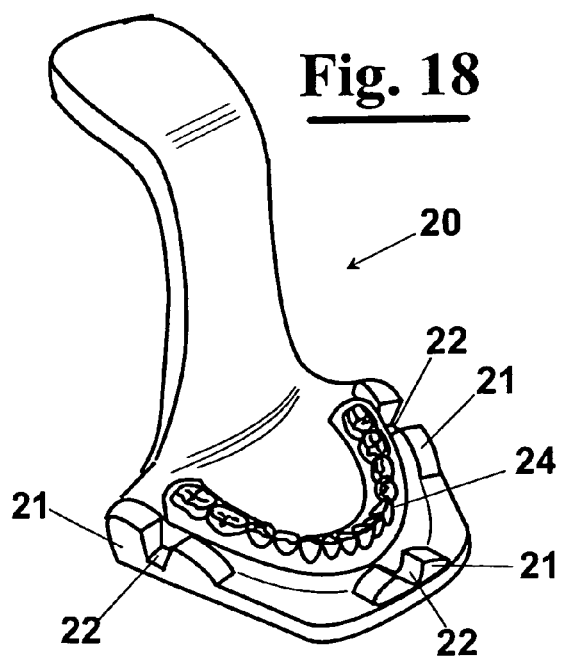

As shown in FIGS. 18 and 19, means can be provided for mutual reference between the model 20 and the semifinished product, both in the case of a plate member 30, and in the case of a pre-printed semifinished product 130, in order to assist a precise location. More in detail, in case of plate member 30, model 20 has pins 23 that engage with housings 32 made in the lower surface of plate member 30 (FIG. 19).

In case of a pre-printed semifinished product 130, instead, model 20, at the molar and the incisors of the dental arch, has protruding parts 21 having cuts 22 in which the protruding wings 136 are arranged of the pre-printed semifinished product 130 (FIG. 20).

Furthermore, as shown in detail in FIG. 21, container 10 and model 20 have respective reference surfaces 11 and 29 suitable to ensure a precise relative positioning. More in detail, container 10 and standard model 20 have frustoconical sections mutually coupled that perform a precise autocentering action.

Figure 22:
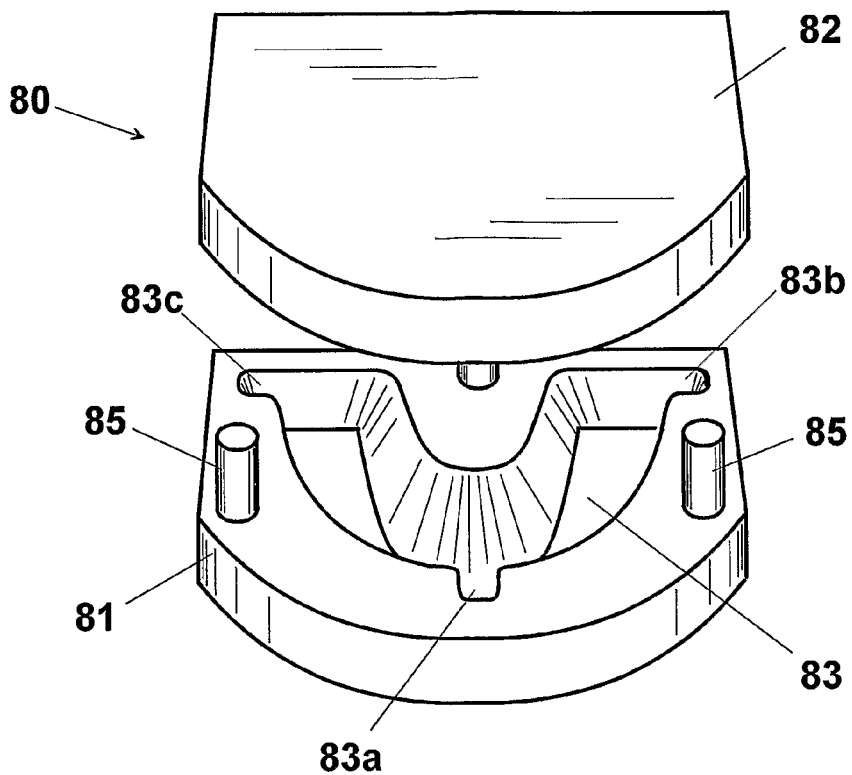
FIGS. 22 and 23 show a perspective elevation front view of a possible exemplary embodiment for mould that can be used to obtain a pre-printed semifinished product, according to the invention.
Figure 23:
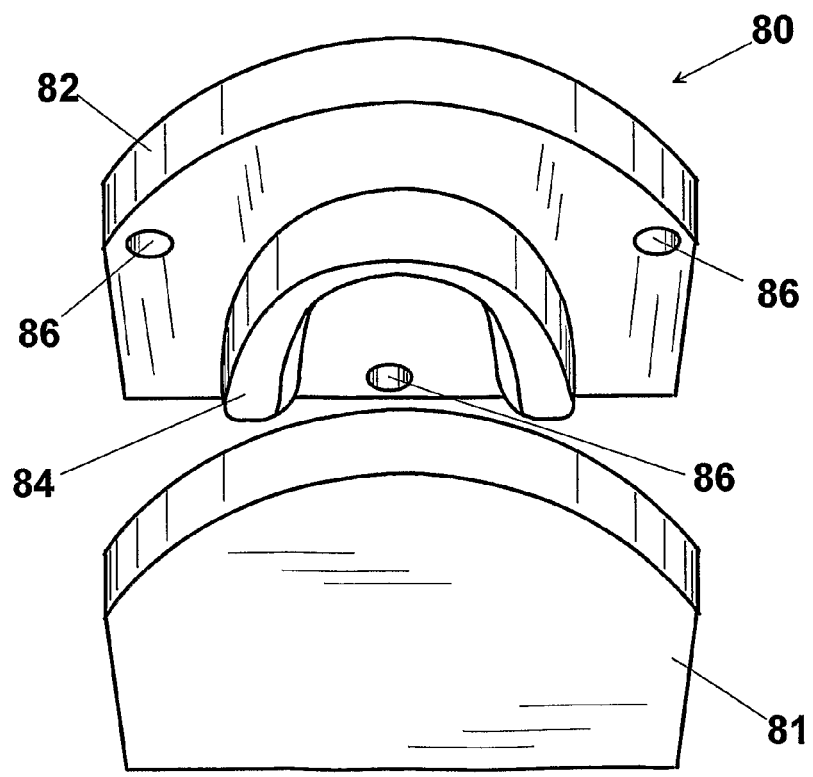

As shown in FIGS. 22 and 23 the pre-printed semifinished product can be obtained using a mould 80 comprising a first half 81 equipped with a housing 83 substantially U-shaped and a second half 82 equipped with a projection 84 which is also substantially U-shaped. In use, the two halves 81 and 82 are overlapped in order to arrange the projection 84 at the housing 83 in which a determined amount of thermoformable material is put in the molten state, which by cooling hardens thus obtaining pre-printed semifinished product 130.

In particular, housing 83, at the central and of the end part, has respective side ends 83a, 83b and 83c at which thermoformable material, once hardened, achieves corresponding wings protruding externally from pre-printed semifinished product 130 extracted from mould 80.

The moulding step of article 130 can be carried out also by a known technology of the injection moulding. In this case, the mould 80 has an opening through which is injected in housing 83 the material in the sted fuso, solution not shown in the figures advantageously.

Furthermore, mutual engagement means can be provided, for example pins 85 and holes 86 made on the two halves 81 and 82 to ensure a correct relative location.

During the moulding step above described in the thermoformable material a retention element can be inserted having a grip portion for the impression of the material. In particular, the grip portion, once made the pre-printed semifinished product 130, remains visible and increases remarkably the capacity of retention of the impression material, as shown in FIGS. 24-27.

More in detail, to cause grip portion on the surface to prepare pre-printed semifinished product 130 a step can be provided of finishing consisting for example of a sandblast process.

Figure 24:
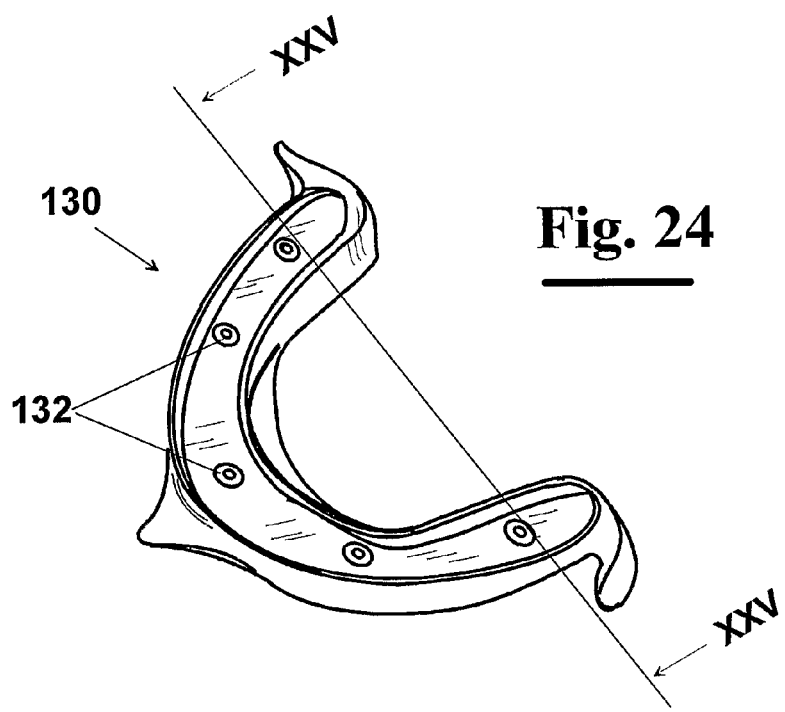
FIG. 24 shows a perspective view of an impression tray, according to the invention, having a grip portion used for increasing the capacity of retention with respect to the impression material.
Figure 25:
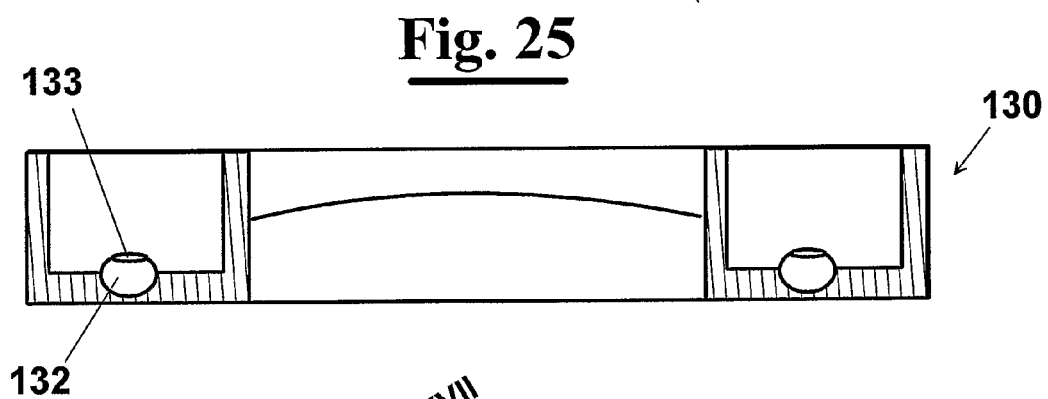
FIG. 25 shows, in a cross section according to arrows XXV-XXV, the impression tray of FIG. 24.

The grip portion can be made at stiff inserts, for example balls 132 having recesses 133, in which the impression material is introduced increasing retention (FIGS. 24 and 25).

Figure 26:
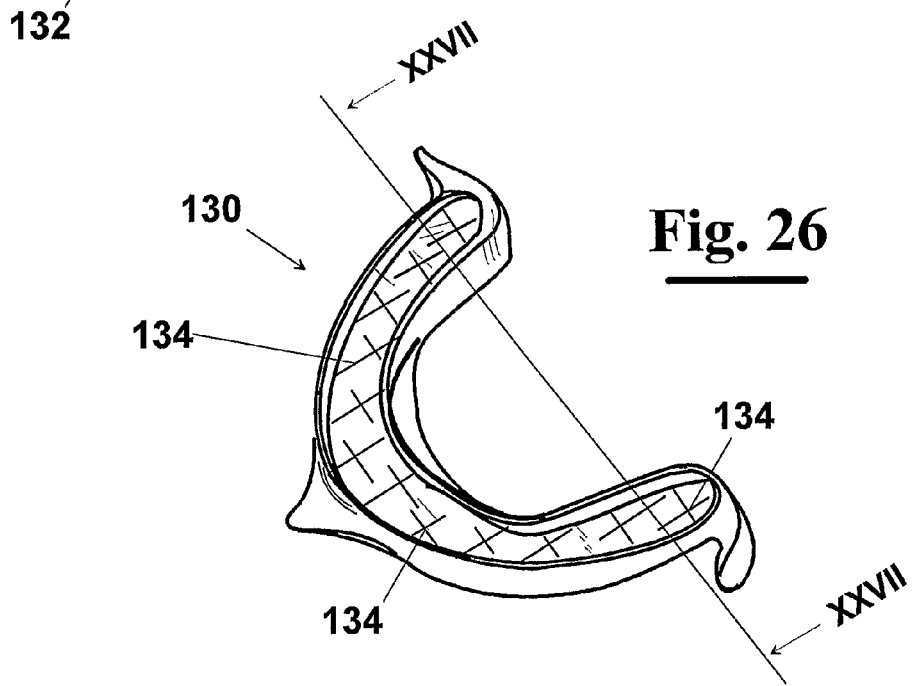
FIG. 26 shows the impression tray, according to the invention, having a grip portion alternative to that of FIG. 24.
Figure 27:
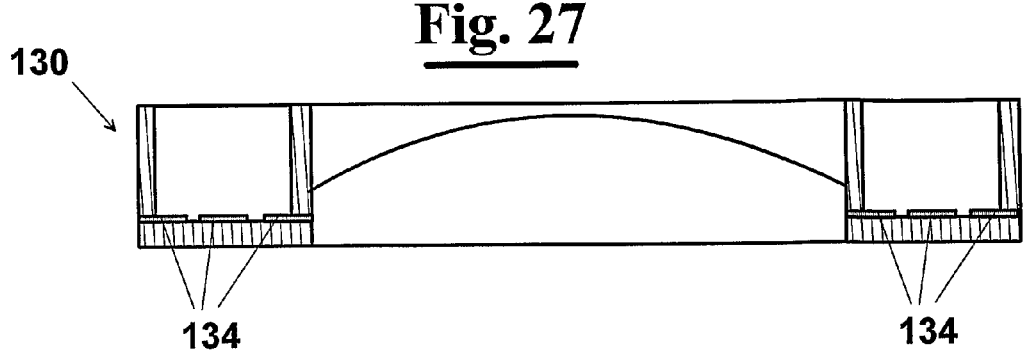
FIG. 27 shows, in a cross section according to arrows XXVII-XXVII, the impression tray of FIG. 26.

Alternatively, the grip portion can be made at portions of fibres 134 arranged according to the mass of the semifinished product 30. In particular, the portions of fibres can be of woven fabric, non woven fabric, knitted fabric, or a different material having a desired rate of porosity (FIGS. 26 and 27).

Figure 28:
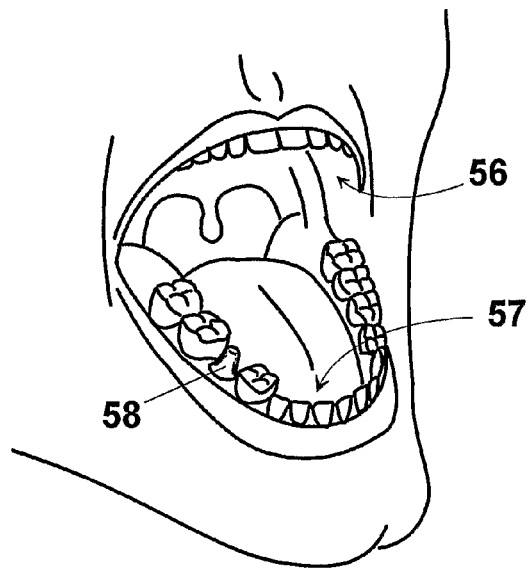
FIG. 28 shows the lower dental arch of a patient on which a milled tooth, or tooth stump, has been made for receiving an artificial part for example a crown, a bridge, etc.
Figure 29A:
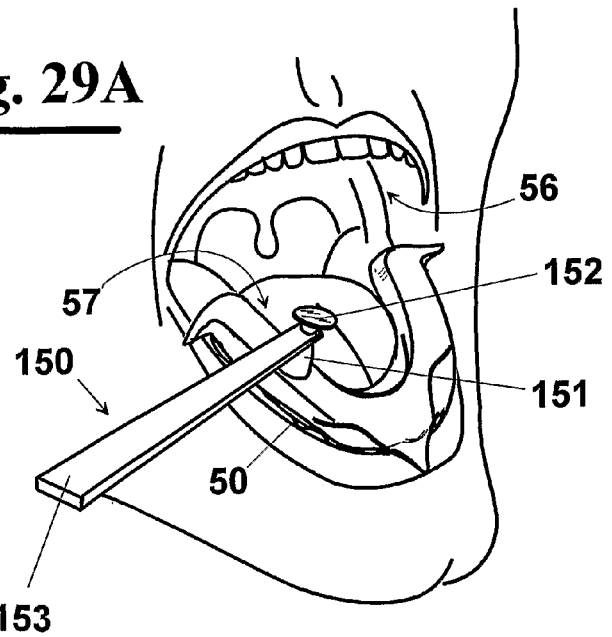
FIG. 29A shows the dental arch of FIG. 28 on which the impression tray has been arranged, according to the invention, and an auxiliary push element of the invention to assist detecting the impression in particular, in case of tooth stumps.
Figure 29B:
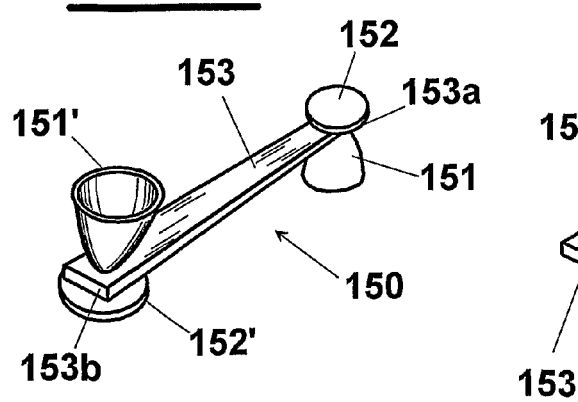
FIG. 29B shows a possible exemplary embodiment of the auxiliary push element of FIG. 29A.

In case of presence of milled teeth, or tooth stumps 58, set to receive artificial articles such as crowns, or bridges, on the dental arch of which an impression has to be obtained (FIG. 28), the kit, according to the invention, can comprise an auxiliary push element 150 (FIGS. 29A and 29B).

Figure 30:
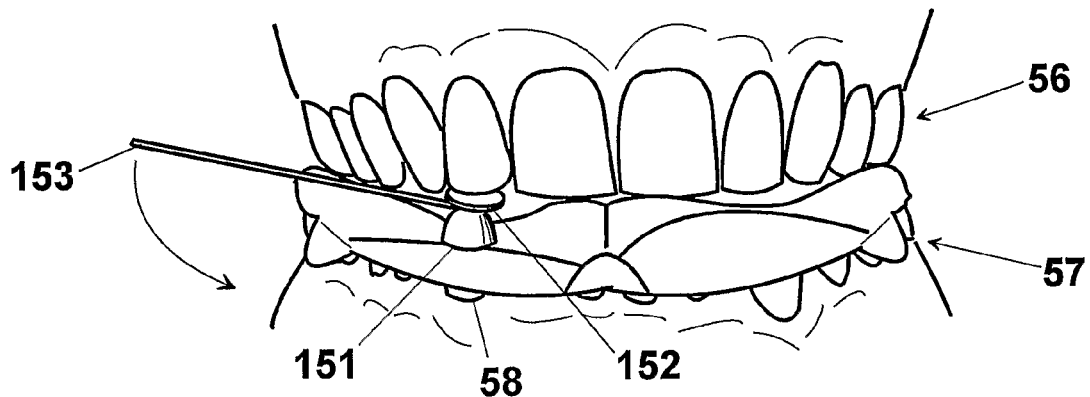
FIGS. 30 to 32 show some steps of obtaining an impression on the dental arch of FIG. 28 by the device shown in FIG. 29.

This, in use, is arranged between the impression tray 30 located with the impression material 50 on the dental arch, for example the lower arch 57, and the dental arch of the patient not interested by the impression material, in FIG. 29A the upper dental arch 56. In particular, as shown in FIG. 29B, the auxiliary push element 150 comprises a hollow body 151, for example C-shaped, which in use moves externally to the tooth, or tooth stump 58, of the dental arch 57. The hollow body 151 is then pivotally connected to a push surface, for example obtained on a rotatable plate 152, on which the dental arch 57 acts while obtaining an impression by pushing the hollow bodies 151 on the impression tray (FIG. 30).

Figure 31:
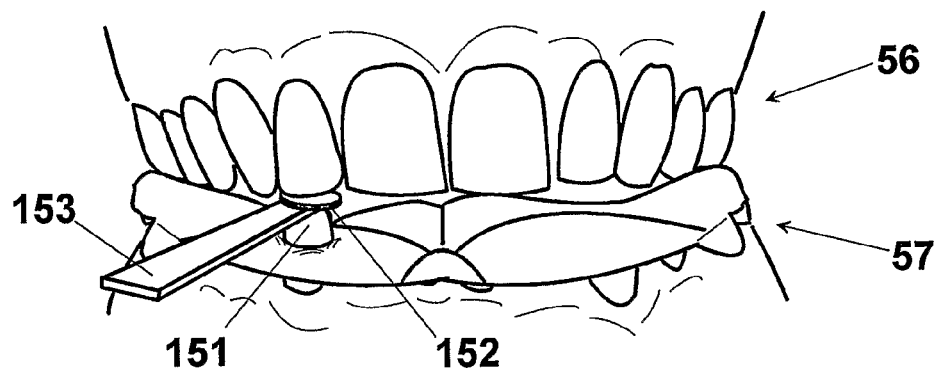

The auxiliary push element 150 has, furthermore, a manoeuvring stick 153 (FIG. 29B), which can be equipped with a handgrip, integral to the hollow bodies 151, that is held by the operator for actuating the push element 150, when obtaining an impression to ensure a correct operation, i.e. an effective push of the impression material 50 towards the base, for all the side surface of the tooth 58, and bringing it then in a position of not encumbrance, FIG. 31.

Figure 32:
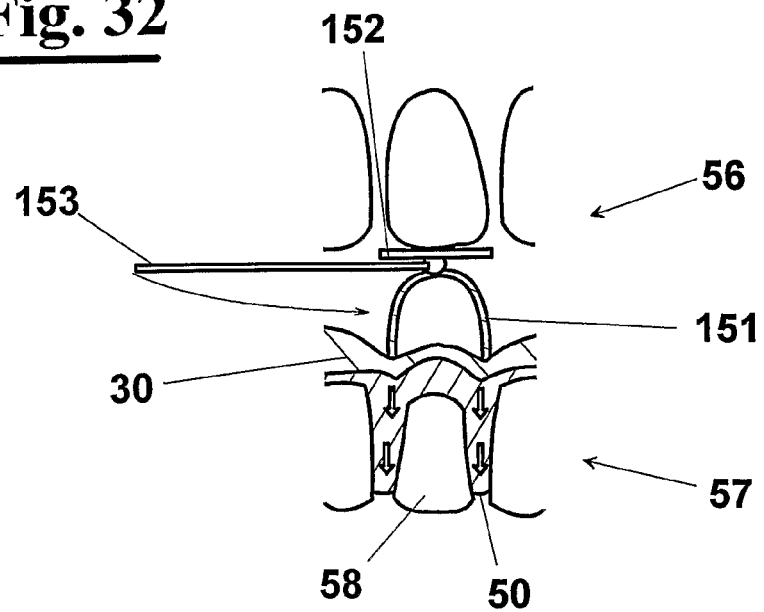

During use, as diagrammatically shown in FIG. 32, the impression material 50 is pressed by the push element 150 towards the base of the tooth stump 58, for obtaining a correct and precise impression. In the presence of tooth stumps 58, in fact, the push of the "free" dental arch by the impression tray 30 on the dental arch 57 of which an impression has to be obtained is not enough to ensure that the impression material 50 it reaches at the base of the tooth. Therefore, the impression drawn at the tooth stump 58 is not precise.

As diagrammatically shown in FIG. 29B, the auxiliary push element 150 has a first hollow object 151 at one end 153a of the manoeuvring stick 153, and another hollow body 151' at the opposite ends 153b. In particular, the hollow bodies 151 and 151' have different size to allow the use of a same auxiliary element 150 for treating the teeth, or tooth stumps, of different size.

As shown in FIGS. 33 and 34, respectively a perspective view from below of and a perspective view from the above of the kit, according to the invention, furthermore, a spacing element 200 can be provided, that, in use, is located between the semifinished product of thermoformable material 30 and the dental arch, for example the upper dental arch 56 (FIG. 35). The spacing element 200 has in detail a base portion 208, substantially U-shaped, and a side portions 209 of a measured height.

The spacing element 200 can be of plastic material, for example polyethylene, or natural rubber, which can be mixed with other compounds to obtain a compound of the type used for chewing gum, or tinfoil, or ALCANTARA® polyester/polyurethane composite textile material.

In particular, before modelling the semifinished product 30 directly on the dental arch 56, the spacing element 200 is arranged on the dental arch of the patient, or arranged in the semifinished product 30, for separating thermally the dental arch and the semifinished product 30. This way, it is avoided that the thermoformable material of which the semifinished product 30 is composed can enter into contact, still hot, with the dental arch, or with the gingivae of the patient.

Furthermore, the presence of the spacing element 200 allows to optimize the thickness of the impression material available 50 during the following step of obtaining the impression.

The base portion 208 of the spacing element 200 can be equipped with reference areas 201, for example defined by tear-off lines 205, arranged at determined points of the dental arch.

Before arranging the spacing element 200 on the dental arch of the patient or in the semifinished product 30, the operator removes, in this case, determined reference areas 201, for example, areas 201b and 201c, corresponding to the position of a rear tooth, one on the right and one on the left, such as the teeth between fourth and the eight. For example, the operator can remove reference areas 201 of base portion 208 using a not shown. Similarly, is withdrawn an area of reference 201 corresponding to the portion of a tooth of the front part of the dental arch, for example the area of reference 201a corresponding to the first front. Then, the thermoformable material once brought to a temperature higher than the softening temperature is arranged above spacing element 200. This way, it can be forced to cross the spacing element 200 at the apertures 207a-207c left by the removed reference areas 201a-201c. Therefore, at the apertures 207a-207c of the spacing element 200, respective projections 31a-31c are formed that protrude from the base of the recess 38 of the semifinished product 30.

When obtaining an impression, the semifinished product 30, already without spacing element 200, enters into contact with the dental arch 56 only at the projections 31a-31c, whereas the volume previously occupied by the spacing element 200 can be used as volume useful to the impression material.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. A method for making an individual impression tray for obtaining an impression of a dental arch comprising the steps of:
   arranging in a container:
   a model of a material selected from the group consisting of a ceramic material and a glass material reproducing a dental arch;
   a semifinished product of thermoformable material located above the model at the dental arch;
   a heat-transmission fluid such that the model and the semifinished product are dipped in said fluid;
   softening the thermoformable material of said semifinished product by heating said fluid at a temperature higher than the temperature for softening said material, said softening step causing the semifinished product to become thermoformed on the model, obtaining a recess on the side of the semifinished product next to the dental arch of the model and a protrusion on the opposite side;
   cooling the thermoformable material to obtain the individual impression tray;
   wherein said pre-printed semifinished product is finished, by modelling said pre-printed semifinished product directly on the dental arch of the patient obtaining an individual impression tray; and
   wherein before finishing the semifinished product of thermoformable material by modeling said semifinished product of thermoformable material on a dental arch of the patient, a step is provided of spraying a surfactant on the dental arch.

2. A method according to claim 1, wherein said model has a handgrip adapted to assist the grip by a specialist, said handgrip, in use, protruding from said container.

3. A method according to claim 1, wherein said dental arch of said model comprises a plurality of templates of teeth that are oversized 20%-30% with respect to the average anatomical size, in order to leave enough space to the impression material.

4. A method according to claim 1, further comprising at least one of the following steps:
   making at least one wing protruding from the external side surface of said pre-printed semifinished product;
   making stiffening beads obtained by folding the borders of said pre-printed semifinished product;
   making lateral containing edges at said projection of said pre-printed semifinished product.

5. A method according to claim 4, wherein said step of making at least one externally protruding wing that protrudes from said side surface of said pre-printed semifinished product provides at least one of the following steps:
   making at least one wing at a portion in front of the incisors;
   making at least one second wing at a portion in front of the right molars;
   making at least one third wing at a portion in front of the left molars.

6. A method according to claim 1, wherein said pre-printed semifinished product is substantially U-shaped, and comprises a recess on one side and a protrusion on an opposite side, and at least one among an externally protruding wing and a lateral containing edge at said projection.

7. A method according to claim 1, wherein said pre-printed semifinished product comprises at least one grip portion that in use remains visible; and wherein said grip portion holds the impression material during the removal of said impression tray from the dental arch of the patient, at the end of the step of obtaining the impression, to increase the capacity of retention of the individual impression tray.

8. A method according to claim 7, wherein said grip portion is made of at least one stiff insert integrated in said thermoformable material; and wherein said grip portion has an external surface that is not harmful to the teeth of the patient.

9. A method according to claim 7, wherein said grip portion comprises a material selected from the group consisting of woven fabric, non-woven fabric, knitted fabric, a material having a determined rate of porosity, and a combination thereof.

10. A method according to claim 1, wherein the model is made from a ceramic material.

11. A method according to claim 1, wherein the model is made from a glass material.

12. A dental kit to make an individual impression tray for obtaining an impression of a dental arch, said kit comprising:
   a standard model of a material selected from the group consisting of a ceramic material and a glass material reproducing a dental arch;

a semifinished product of thermoformable material adapted to be put on said standard model at said dental arch;

a container adapted to contain a heat exchange fluid in which said semifinished product and said model are put, for being heated together; and a spacing element comprising a substantially U-shaped plate member and a side portion having a measured height, said spacing element being adapted, in use, to be located between the dental arch of which an impression has to be obtained and said semifinished product of thermoformable material;

wherein said spacing element has areas defined by tear-off lines that assist in removing the tray, said areas corresponding to determined points of said dental arch, whereby removing at least one part of said reference areas, corresponding apertures are formed before arranging said semifinished product and said spacing element on said dental arch of said patient, said thermoformable material of said semifinished product further comprising projections which rest on said dental arch and crossing said spacing element only at said apertures.

13. A kit according to claim 12, comprising, furthermore, a source of thermal power adapted to cause said fluid to heat up to a temperature higher than the softening temperature of said thermoformable material.

14. A kit according to claim 12, wherein said container and said standard model have respective reference surfaces suitable to ensure a precise relative location said surfaces having frustoconical sections that can be mutually coupled.

15. A kit according to claim 12, wherein said standard model and said semifinished product have mutual cooperating means adapted to assist the mutual positioning.

16. A kit according to claim 12, wherein said semifinished product is made of a material for prosthetic bases selected from the group consisting of:
polymethylmethacrylate (PMMA);
acrylic resins,
vinyl-acrylic copolymers,
urethane oligomers,
shellac, which can be added to a mixture of copal, colophony, natural resins and synthetic resins, and
a combination thereof.

17. A kit according to claim 12, wherein said semifinished product is selected from the group comprised of:
a plate member, which can be U-shaped;
a pre-printed semifinished product;
a substantially U-shaped pre-printed semifinished product having a recess on one side and a protrusion on the opposite side, characterised on having at least one among:
an externally protruding wing;
a lateral containing edge at said projection.

18. A kit according to claim 12, wherein said spacing element is made of a material selected from the group consisting of:
pluriball;
rubber;
tinfoil; and
a polyester/polyurethane composite textile material.

19. A kit according to claim 12, wherein a container is provided having a temperature sensor adapted to measure the temperature of the fluid in the container and to send a corresponding signal of temperature to a device adapted to determine the heating time necessary for bringing said fluid from a starting temperature to a determined temperature higher than the temperature for softening said material, by a determined source of thermal power.

20. A kit according to claim 12, wherein an auxiliary push element is provided that is arranged, in use, between said impression tray put, with said impression material inside, on the dental arch of which an impression has to be obtained and the other dental arch, said auxiliary push element being pressed when closing the mouth of the patient against the impression tray in order to force the impression material towards the base of the dental arch.

21. A kit according to claim 20, wherein said auxiliary push element comprises:
hollow bodies adapted to contain at least one tooth, or tooth stump, of the dental arch;
a push surface on which the dental arch not interested by the impression material acts for pushing said hollow bodies on said impression tray, said push surface and said hollow bodies being pivotally connected to each other;
a handgrip integral to said hollow bodies and adapted to be gripped by the operator for actuating said hollow bodies.

22. A kit according to claim 12, wherein the model is made from a ceramic material.

23. A kit according to claim 12, wherein the model is made from a glass material.

24. An individual impression tray for obtaining an impression of a dental arch, produced according to the method of claim 1.

* * * * *